(12) United States Patent
Hashmi et al.

(10) Patent No.: US 7,692,039 B2
(45) Date of Patent: Apr. 6, 2010

(54) PROCESS FOR PREPARING PURIFIED TEREPHTHALIC ACID

(75) Inventors: Syed Mohammed Azhar Hashmi, Riyadh (SA); Sulaiman Al-Luhaidan, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 11/793,288

(22) PCT Filed: Dec. 9, 2005

(86) PCT No.: PCT/IB2005/003722

§ 371 (c)(1),
(2), (4) Date: Feb. 4, 2008

(87) PCT Pub. No.: WO2006/085134

PCT Pub. Date: Aug. 17, 2006

(65) Prior Publication Data

US 2008/0275271 A1  Nov. 6, 2008

(30) Foreign Application Priority Data

Dec. 15, 2004  (EP) .................................. 04029615

(51) Int. Cl.
*C07C 51/42* (2006.01)
(52) U.S. Cl. ........................ 562/486; 562/414; 562/485; 562/416
(58) Field of Classification Search ................. 562/414, 562/485, 486, 404, 416, 77
See application file for complete search history.

(56) References Cited

U.S. PATENT DOCUMENTS

| | | | | |
|---|---|---|---|---|
| 5,095,145 A | * | 3/1992 | Rosen | 562/483 |
| 5,567,842 A | * | 10/1996 | Izumisawa et al. | 562/486 |
| 5,583,254 A | * | 12/1996 | Turner et al. | 562/414 |
| 5,723,659 A | * | 3/1998 | White | 562/485 |
| 5,840,965 A | | 11/1998 | Turner et al. | |
| 2002/0193630 A1 | | 12/2002 | Lin et al. | |

FOREIGN PATENT DOCUMENTS

EP  1338318  8/2003

* cited by examiner

*Primary Examiner*—Porfirio Nazario-Gonzalez
*Assistant Examiner*—Yate' K Cutliff
(74) *Attorney, Agent, or Firm*—Jim Wheelington

(57) ABSTRACT

The present invention relates to a process for preparing purified terephthalic acid [PTA,], comprising the steps: dissolving crude terephthalic acid [CTA] in an aqueous medium in a reactor; hydrogenating CTA at a temperature of about 260-320° C. and a pressure of about 1100-1300 psig using a hydrogenation catalyst; crystallizing terephthalic acid in the reactor by lowering the temperature of the solution to about 160° C. without evaporation cooling; transferring the content of the reactor to a filtration unit; filtrating the content at a temperature of about 140-160° C. and a pressure of about 40-100 psig, preferably 80-100 psig to obtain a filter cake, washing the filter cake obtained with water having a temperature of about 140-160° C. in the filtration unit; and drying the filter cake.

15 Claims, 2 Drawing Sheets

Fig. 1: Comparison of 4-CBA contents
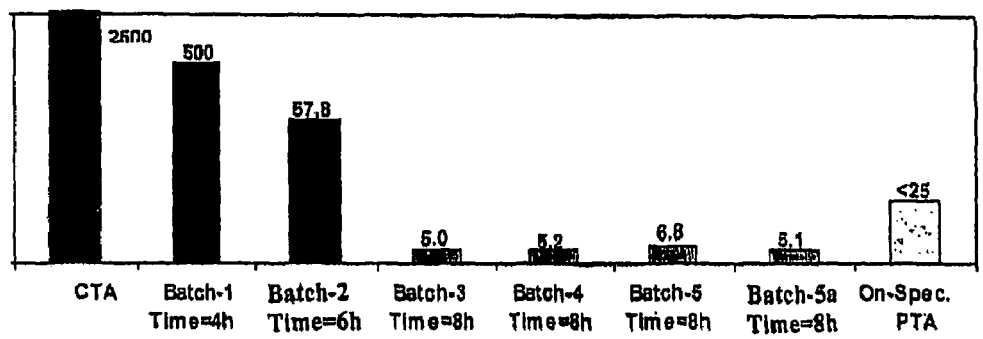
Fig. 2: Comparison of p-Toluic contents
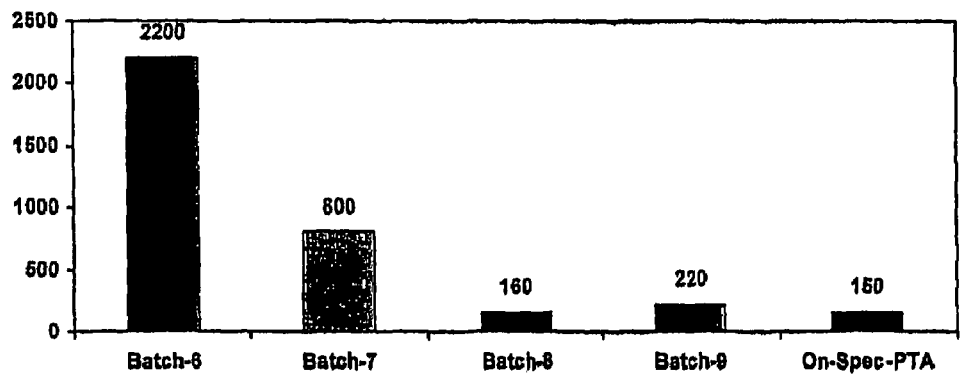
Fig. 3: Comparison of p-Toluic acid
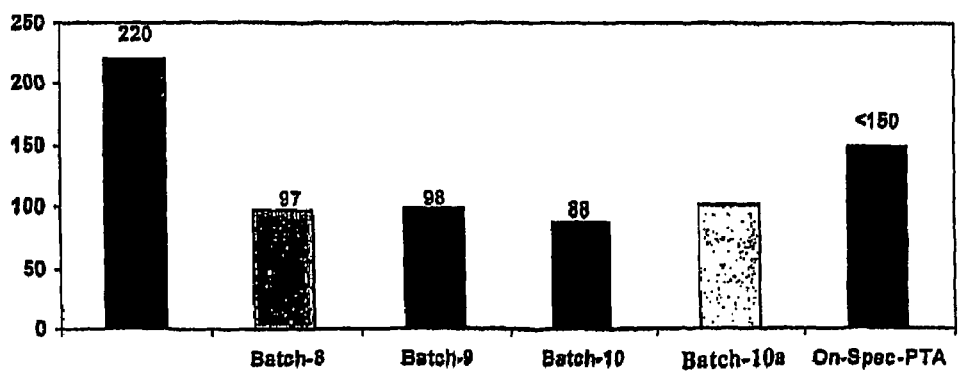

Fig. 4: Comparison of Metal Contents
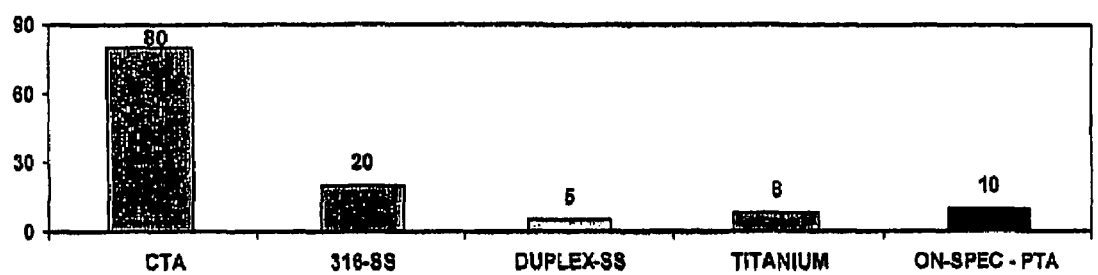
Fig. 5: Comparison of Color Properties
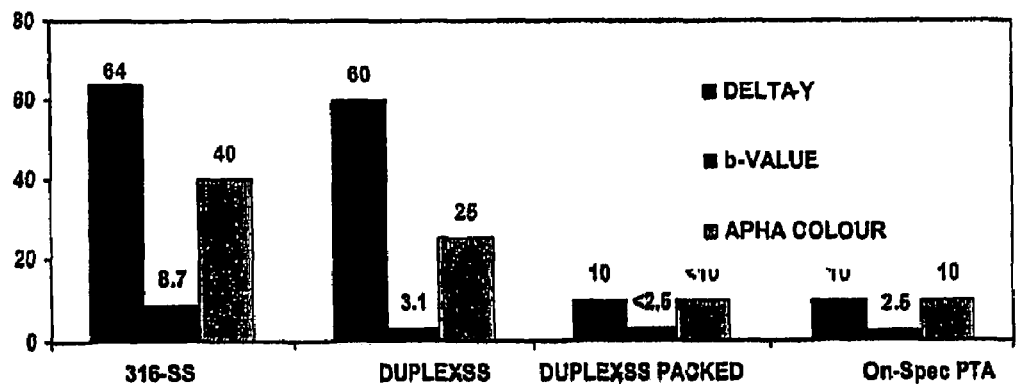

PROCESS FOR PREPARING PURIFIED TEREPHTHALIC ACID

The present invention relates to a process for preparing purified terephtalic acid.

Purified terephtalic acid (PTA) is a commodity petrochemical of great commercial importance. It is used as a key raw material for the production of various types of polymers. The world production capacity for PTA is above 25 million metric tons per year. Polymer grade or purified terephthalic acid is the starting material for polyethylene terephthalate, which is the principal polymer for polyester fibres, polyester films, and resins for bottles and the like containers. Purified terephthalic acid is produced commercially from relatively less pure, technical grade or crude terephthalic acid (CTA). Crude terephthalic acid may be obtained by oxidation of p-xylene usually containing relatively large amounts of various impurities. Such impurities may include the following. The organic impurities present in CTA include partially oxidized products, such as 4-carboxybenzaldehyde (~3000 ppm) and p-toluic acid (~500 ppm) being a hydrogenation product of 4-carboxybenzaldehyde. Color impurities may include benzil, fluorenone and/or anthraquinone (~30 ppm). Metal impurities include iron and other metals (~85 ppm). In addition, moisture (~0.2%) and ash (~100 ppm) may be present as impurities. Table-1 below shows the specification of crude and pure terephthalic acid. The specification of PTA is the one which is necessary to be useful as starting material for polymerization

TABLE 1

Specification of CTA and PTA

| PROPERTY | UNITS | CTA | PTA |
|---|---|---|---|
| Purity | % | 99.7 | 99.95 |
| 4-CBA | ppm | 2500 | <25 |
| P-Toluic Acid | ppm | 500 | <150 |
| APHA Color | HU | 50 | <10 |
| Δ Y | | 30 | <10 |
| b-Value | | 9 | <2.5 |
| ASH | ppm | 100 | <10 |
| Moisture | % | 0.2 | <0.1 |
| Total Metals | ppm | 85 | <10 |

PTA may be commercially produced by catalytic hydrogenation of the intermediate crude terephthalic acid over palladium catalyst supported on carbon. The hydrogenation reaction is performed in an aqueous solvent at high temperature of 280° C. and high pressure of 80 bar. This is followed by crystallization, hot filtration hot washing and drying to obtain PTA having a purity of more than 99.95%

U.S. Pat. No. 5,567,842 discloses a process for producing pure terephthalic acid, wherein the hydrogenation step is carried out in a continuous fixed bed reactor, whereupon the slurry is fed to multiple crystallizers wherein the temperature is lowered stepwise by pressure release cooling.

U.S. Pat. No. 3,584,039 discloses a process for producing pure terephthalic acid in a batch reactor. Again, the hydrogenation reactor is cooled by releasing the pressure which vaporizes water from the solution and cools the solution, thereby precipitating terephthalic acid crystals. The obtained terephthalic acid crystals are filtered at room temperature.

Moreover, U.S. Pat. No. 5,767,311 discloses a method for purifying crude terephthalic acid from a liquid dispersion thereof, wherein the method does not include a hydrogenation step, but the crude terephthalic acid is only purified by crystallization and filtration steps.

The known processes for preparing pure terephthalic acid are connected with the disadvantages that, mostly, the catalytic hydrogenation of CTA is carried out in a fixed bed and requires low concentration of feed. Further, hydrogenation and crystallization are often performed separately in different reactors, and also several stage crystallization is common. Additionally, crystallization is performed by evaporation cooling (depressurisation) of the water solvent which results in build-up on the wall of crystallization reactors. Finally, also hot filtration and hot washing is often done separately and by reslurrying solid product obtained after hot filtration. Therefore, loss of material occurs and also load on waste water and energy.

It is an object of the present invention to provide a process for preparing pure terephthalic acid which overcomes the drawbacks of the prior art.

This object is achieved by a process for preparing purified terephthalic acid (PTA), comprising the steps:

i) dissolving crude terephthalic acid (CTA) in an aqueous medium in a reactor;

ii) hydrogenating CTA at a temperature of about 260-320° C. and a pressure of about 1100-1300 psig using an hydrogenation catalyst;

iii) crystallizing terephthalic acid in the reactor by lowering the temperature of the solution to about 160° C. without evaporation cooling;

iv) transferring the content of the reactor to a filtration unit;

v) filtrating the content at a temperature of about 140-160° C. and a pressure of about 40-100 psig, preferably 80-100 psig to obtain a filter cake;

vi) washing the filter cake obtained with water having a temperature of about 140-160° C. in the filtration unit; and vii) drying the filter cake.

Preferably, the process is carried out in a batch reactor.

Still preferred, in steps i)-iii) the reactor content is agitated with a stirrer at about 250-400 rpm.

In one embodiment, within the reactor a basket is disposed containing the hydrogenation catalyst.

Preferably the basket is made of titanium or duplex-stainless steel.

It is further preferred that the hydrogenation catalyst contains a platinum group metal selected from the group consisting of palladium, ruthenium, rhodium, osmium, iridium, and platinum, or an oxide of such a metal.

It is preferred that the hydrogenation catalyst is supported on a carrier.

Most preferred the hydrogenation catalyst is palladium on a carrier of active carbon.

In one embodiment, the aqueous medium is water, preferably demineralized water.

Further, it is advantageous that the time for hydrogenation in step i) is at least six hours, preferably at least seven hours, most preferably at least eight hours.

It is preferred that in step ii) the lowering of the temperature is done at a rate of about 1° C./min, to a temperature of about 160° C.

Most preferably, after a temperature of about 160° C. in step iii) has been reached, the reactor is depressurized by evaporation to a pressure of about 100 psig.

Still preferred is that the temperature is maintained after the temperature of about 160° C. has been reached.

In one embodiment the transfer in step iv) is done via a transfer line which is kept at a temperature of about 180-250° C.

It is advantageous that the water used in step vi) is heated in the reactor at a pressure of about 100 psig.

It is still preferred that in step ii) lowering of the temperature is achieved by passing coolant through coolant circulation coils disposed at and/or in the reactor.

Preferably, the coolant is water, preferably chilled water having a temperature of about 10-15° C.

Finally, it is preferred that the content of PTA in step i) is between about 5-60 weight percent, based on the total weight of PTA and aqueous medium.

Surprisingly, it was found for the process of the present invention that several advantages may be achieved, if the process utilizes the following steps:
crystallizing the terephthalic acid in the hydrogenation reactor by lowering the temperature without evaporation cooling to a temperature of about 160° C., and
transferring the content of the hydrogenation reactor to a unit where both filtration and washing may be carried out. Further, it is advantageous to utilize a continuously stirred hydrogenation reactor in contrast to the fixed bed reactor used in the prior art.

As the cooling of the hydrogenated terephthalic acid solution is performed via a lowering of reaction temperature and not by depressurizing, no build-up on the wall of the hydrogenation reactor is observed. Further, hot filtration and hot washing is carried out in one filtration unit without reslurrying the solid product obtained, so that the loss of material may be controlled.

As outlined above, the cooling for crystallization is effected only by lowering the temperature and not by depressurization. However, during cooling the pressure is automatically lowered to about 250-300 psig. After a cooling temperature of about 160° C. is obtained, the pressure may then preferably be lowered further by depressurizing to 100 psi. This avoids shock cooling and produces a product having good quality, articles with good morphology and a product with high purity. The particle size distribution of the PTA is narrow with few fine (dust) particles. The particles also have good strength. Further, a depressurization at a lower temperature has other advantages, such as a carry over of crystals to the vent line is prevented, thus avoiding blockages which is a common problem with some commercial plants.

It is also preferred that the temperature of the transfer line is kept higher than the temperature of the crystallization reactor and the hot filtration unit. This avoids plugging as a result of flash cooling in the transfer line.

Additional advantages and features will become apparent from the following detailed description of examples for a process for preparing pure terephthalic acid, with reference to the accompanying drawings, wherein:

FIG. 1 shows a comparison of 4-carboxybenzaldehyde contents using different hydrogenation times in a process of the present invention;

FIG. 2 is a comparison of p-toluic acid contents after hot filtration in a process of the present invention;

FIG. 3 is a comparison of p-toluic acid contents after hot washing in a process of the present invention;

FIG. 4 is a comparison of metal contents using different metals as material for the catalyst basket within a process of the invention; and FIG. 5 is a comparison of color properties of pure terephthalic acid obtained by a process of the present invention.

Chemicals: The quantity and source of the chemicals used in each batch carried out for the conversion of CTA to PTA are as follows: a hydrogenation reaction was performed in a hydrogenation reactor using 1.25 kg of commercial CTA and 32 gm of palladium catalyst on a carbon support (commercially available from Sud-Chemie or Engelhard). The purity of hydrogen gas used was 99% and demineralised water of specific conductance of less than 1 was used.

Feed preparation: A feed mixture for hydrogenation reaction was prepared by feeding first water into the reactor by applying vacuum. This was followed by manual addition of 1.25 kg of CTA powder to the reactor using a funnel. This mixture was then agitated at 320 rpm to give a slurry containing about 13.5 weight percent of terephthalic acid. Nitrogen gas was then added to the reactor twice up to 50 psig and the reaction mixture was agitated for 5 minutes, and then the gas was released by opening a vent valve, keeping a nitrogen pressure of 10 psig in the reactor. Inside the hydrogenation reactor a catalyst basket containing the hydrogenation catalyst is fixed, for example at a cooling coil within the reactor.

Hydrogenating: Hydrogenation of CTA to convert the main impurity of 4-carboxybenzaldehyde (4-CBA) into p-toluic acid was carried out at a temperature of 285° C., and the pressure of the reactor was maintained at 1200 psig, i.e. above the partial pressure of water to maintain a liquid phase and to ensure an adequate supply of hydrogen. The hydrogenation reaction was carried out for different time periods, during which hydrogen was supplied, when the pressure decreased and reached the partial pressure of water, in order to keep the pressure almost constant.

Crystallizing: After the time period of the hydrogenation reaction was over, the beater of the hydrogenation reactor was switched off, and the temperature of the reactor was lowered to 160° C. by passing chilled water of a temperature of about 10-15° C. through water circulation coils at and/or in the hydrogenation reactor. In general, the decrease in temperature is very slow at a rate of about 1° C. per minute. During the crystallization the agitator was kept on at 320 rpm. When a temperature of 160° C. was reached the heater was switched on again to avoid further lowering of the temperature. After a temperature of 160° C. was reached, depressurization was carried out to bring the reactor pressure to about 100 psi. Depressurization at this temperature will not result in a significant loss of PTA product, but only hydrogen gases that were added to built up the pressure, will be released.

Hot filtrating: The hot filtration for removing p-toluic acid from an aqueous slurry of terephthalic acid was carried out using a Sparkler filter unit. Nitrogen gas was first flushed through the filter unit and a pressure of about 80 psig was kept in the filtration unit. The content of the reactor was then transferred via a transfer line to the filtration unit. The content of the reactor was fed continuously, however, the pressure in the filter unit was maintained at 80 psig by slowly controlling a drain valve of the hydrogenation reactor. The filtration unit was kept at a temperature of about 140-160° C., and the transfer line was kept at a temperature of about 180-200° C.

Hot washing: About 6 litres of demineralised water was heated to a temperature of 160° C. in the hydrogenation reactor. The hot water at a temperature of 160° C. and a pressure of about 100 psig was then fed to the filtration: unit containing the filter cake. The hot water was fed continuously to the filter, however, the pressure in the filter unit was maintained at about 80 psig by controlling the drain valve of the reactor. Also in the washing process, the temperature of the transfer line was kept at a temperature of about 180-200° C.

After the washing process, the filter cake obtained may be removed from the filtration unit and/or may be dried to dryness, as desired.

In the following description, possibilities for optimizing the major processing steps to produce pure terephthalic acid having required purity (on-spec PTA) are illustrated.

Optimization of hydrogenation conditions: The major impurity present in CTA is 4-carboxy benzaldehyde. The 4-CBA causes undesirable coloring of the polymer as a consequence of its thermal instability during polymerization. Therefore, parameters for reducing 4-CBA have been studied.

FIG. 1 shows the results of five batches of terephthalic acid obtained in a process of the present invention, carried out by varying the reaction in order to reduce the content of 4-CBA from 2500 ppm (off-spec) to <25 ppm (on-spec).

The hydrogenation reaction in batch-1 and batch-2 was carried out for a period of 4 hours and 6 hours at 285° C. temperature and 1200 psig pressure. The analysis showed that hydrogenation is incomplete in both batches. The 4-CBA content present in the PTA obtained was 500 ppm and about 60 ppm respectively. In batch-2 the content of 4-CBA decreased significantly with increase in reaction time for two hours, but the content was still off-spec. The hydrogenation reaction in batch-3 was carried out for 4 period of 8 hours at 285° C. temperature and 1200 psig pressure. The analysis showed that hydrogenation is complete. The 4-CBA contents present in the PTA obtained was only 5 ppm. The hydrogenation reaction in batch-4, batch-5 and batch-5a was carried out under similar operation conditions as in batch-3 to confirm the optimized parameters obtained. The analysis revealed a 4-CBA content of 5.2, 6.8 and 5.1 ppm for these batches, respectively. Further, it could be demonstrated in additional experiments, that at a pressure below 1110 psi the hydrogenation was incomplete, and the 4-CBA content was higher than 25 ppm. Similar results may be obtained using a temperature outside the range of about 260-320° C.

Optimization of hot filtration condition: A further major impurity present in CTA is p-toluic acid. P-toluic acid acts as polymerization terminator and slows down the polymerization rate and decreases the average molecular weight of the polymer. FIG. 2 shows the results of hot filtration experiments which were carried out for different batches obtained in a process of the present invention, as outlined above.

In batch-6 PTA was obtained without hot filtration and the p-toluic acid content was about 2200 ppm. The transfer line in batch-6 was not heated or heat traced. In batch-7 PTA was obtained by performing hot filtration and the p-toluic acid content was about 800 ppm. In batch-7 the temperature of the transfer line was about 100° C. The analysis showed that the hot filtration is not successful and some amount of p-toluic acid is crystallized with PTA. Batch-8 and batch-9 were carried out in a similar manner except that the transfer line temperature was increased to 220° C. The analysis showed that after the hot filtration the content of p-toluic acid is reduced to 160 and 220 ppm, respectively. These result show that the amended hot filtration is successful and p-toluic acid contents may be reduced significantly.

Optimization of hot washing conditions: In on-spec PTA the p-toluic acid content should be less than 150 ppm. Therefore washing of the PTA cake with hot water was carried out to reduce the amount of p-toluic acid further. FIG. 3 shows the results of hot filtration and hot washing experiments which were carried out for several batches obtained in a process of the present invention. The content of p-toluic acid in batch-8 after hot filtration was 160 ppm and was reduced after hot washing to about 97 ppm. Similarly, the content of p-toluic acid in batch-9 was 200 ppm after hot filtration and was reduced after hot washing to 98 ppm. Likewise, more experiments were carried out by performing both hot filtration and hot washing and the analysis of PTA obtained showed that the content of p-toluic acid is always on-spec (<150 ppm).

Removal of metallic impurities: Metallic impurities act as poison for the antimony catalyst during the polymerization reaction of purified terephthalic acid. In pure terephthalic acid the total metal content should be <10 ppm. FIG. 4 shows the metal analysis of several batches obtained in a process of the present invention using different metal materials as catalyst baskets, namely SS-316, Duplex-SS and Titanium. The PTA obtained showed a very high total metal content with SS-316, as SS-316 is not a suitable material of construction for carrying out a purification process of crude terephthalic acid. The total metal contents was on-spec using titanium and duplex-SS as material for the catalyst basket.

Removal of color impurities: Color impurities present in CTA lower the melting point of polyester and/or cause coloration of the polyester. In fact, some impurities that are contained in the crude terephthalic acid are color-forming precursors. Therefore, the effect of known and potential color impurities on PTA prepared in a batch process according to the present invention, were investigated. Three optical properties, i.e. delta Y, b-value and APHA color were investigated. A delta-Y value of >10, b-value of >2.5 and APHA color value of >10 (HU) indicates that the sample is heavily contaminated and is not a commercially accepted product. FIG. 5 shows results of optical properties, i.e. delta Y, b-value and APHA color for several PTA batches obtained in the process of the present invention using different materials for the catalyst basket. In this regard, duplex is the metallurgy of catalyst basket used during the hydrogenation reaction. The capacity of the basket is bigger than the amount of catalyst used during hydrogenation reaction. Therefore, under high pressure and agitation catalyst pellets move inside the catalyst basket and some get crushed and impart colour to the product. Therefore, the colour of PTA product was affected. In duplex packed basket, some inert material was used to fill the remaining space inside the catalyst basket so that the catalyst pellets were fixed and not moveable.

The features disclosed in the foregoing description, in the claims and/or in the accompanying drawings may, both separately and in any combination thereof, be material for realizing the invention in diverse forms thereof.

The invention claimed is:

1. A process for preparing purified terephthalic acid (PTA), comprising the steps:
   i) dissolving crude terephthalic acid (CTA) in an aqueous medium in a reactor;
   ii) hydrogenating CTA to convert an impurity of 4-carboxybenzaldehyde at a temperature of about 260-320° C. and a pressure of about 1100-1300 psig using an hydrogenation catalyst;
   iii) crystallizing terephthalic acid in the reactor by lowering the temperature without depressurization of the hydrogenated CTA in the aqueous medium to about 160° C. and then, optionally, depressurizing the reactor to 100 psi by release of hydrogen gas;
   iv) transferring the content of the reactor to a filtration unit;
   v) filtrating the content at a temperature of about 140-160° C. and a pressure of about 40-100 psig to obtain a filter cake;
   vi) washing the filter cake obtained with water having a temperature of about 140-160° C. in the filtration unit;
   vii) drying the filter cake
   wherein, in the alternative:
   a) in step iii) lowering the temperature at a rate of about 1° C./min or
   b) in step iii) lowering the temperature by passing coolant through coolant circulation coils disposed at and/or in the reactor or c) after step iii) depressurizing the reactor by evaporations to a pressure of about 100 psig after the temperature of about 160° C. has been reached or d) after step iii) maintaining the temperature after the temperature of about 160° C. has been reached.

2. The process according to claim 1, wherein the process is carried out in a batch reactor.

3. The process according to claim 1, wherein in steps i)-iii) the reactor content is agitated with a stirrer at about 250-400 rpm.

4. The process according to claim 1, wherein within the reactor a basket is disposed containing the hydrogenation catalyst.

5. The process according to claim 4, wherein the basket is made of titanium or duplex-stainless steel.

6. The process according to claim 1, wherein the hydrogenation catalyst contains a platinum group metal selected from the group consisting of palladium, ruthenium, rhodium, osmium, iridium, and platinum, or an oxide of such a metal.

7. The process according to claim 6, wherein the hydrogenation catalyst is supported on a carrier.

8. The process according to claim 7, wherein the hydrogenation catalyst is palladium on a carrier of active carbon.

9. The process according to claim 1, wherein the aqueous medium is water.

10. The process according to claim 1, wherein the time for hydrogenation in step ii) is at least six hours.

11. The process according to claim 1, wherein the transfer in step iv) is done via a transfer line which is kept at a temperature of about 180-250° C.

12. The process according to claim 1, wherein the water used in step vi) is heated in the reactor at a pressure of about 100 psig.

13. The process according to claim 1, wherein in step iii) the temperature is lowered by passing water through coolant circulation coils disposed at and/or in the reactor.

14. The process according to claim 1, wherein the content of PTA in step i) is between 5-60 weight percent, based on the total weight of PTA and aqueous medium.

15. The process according to claim 13 wherein the water is chilled water having a temperature of about 10-15° C.

* * * * *